United States Patent [19]

Speier

[11] Patent Number: 5,175,330
[45] Date of Patent: Dec. 29, 1992

[54] PROCESS FOR THE RECOVERY OF HYDROGEN CHLORIDE AND MONOMERIC ALKOXYSILANES FROM MIXTURES OF CHLORIDE-CONTAINING SILICON COMPOUNDS

[75] Inventor: John L. Speier, Midland, Mich.

[73] Assignee: Dow Corning Corporation, Midland, Mich.

[21] Appl. No.: 914,084

[22] Filed: Jul. 16, 1992

[51] Int. Cl.$^5$ .................................................. C07F 7/18
[52] U.S. Cl. ..................................... 556/468; 556/471
[58] Field of Search .......................................... 556/471

[56] References Cited

U.S. PATENT DOCUMENTS

| | | |
|---|---|---|
| 3,478,078 | 11/1969 | Atwell ................................. 556/468 |
| 3,576,035 | 4/1971 | Atwell ................................. 556/558 |
| 4,471,133 | 9/1984 | Hallgren ............................. 556/471 |
| 4,506,087 | 3/1985 | Fischer .............................. 556/471 |
| 4,827,008 | 5/1989 | Gousetis et al. ................ 556/471 X |

Primary Examiner—Paul F. Shaver
Attorney, Agent, or Firm—Robert L. McKellar

[57] ABSTRACT

Disclosed herein is a process of recovering hydrogen chloride and monomeric alkoxysilanes from mixtures of chlorine-containing silicon compounds wherein waste chlorine-containing silicon compounds, for example, are converted to useful, valuable silicon intermediates.

6 Claims, No Drawings

PROCESS FOR THE RECOVERY OF HYDROGEN CHLORIDE AND MONOMERIC ALKOXYSILANES FROM MIXTURES OF CHLORIDE-CONTAINING SILICON COMPOUNDS

This invention deals with a process of recovering hydrogen chloride and monomeric alkoxysilanes from mixtures of chlorine-containing silicon compounds wherein waste chlorine-containing silicon compounds are converted to useful, valuable silicon intermediates.

BACKGROUND OF THE INVENTION

This invention relates to the handling of mixtures of chlorine-containing compounds and it is especially directed to high boiling products that invariably form during the Direct Syntheses of chlorosilanes. Such materials are called Direct Process Residue Wastes.

The Direct Process provides for the direct synthesis of monomeric chlorosilanes by the reaction of gaseous methyl chloride or hydrogen chloride with elemental silicon in a fluid bed reactor at an elevated temperature. This reaction is catalyzed and optimized to prepare dimethyldichlorosilane, by far the most important intermediate for the preparation of industrial "Silicones". The process is also optimized to prepare trichlorosilane, a very important intermediate to prepare transistor grade silicon and many organotrichloro-silane intermediates.

There is created in the Direct Process, a residue, which is obtained after distillation of the dimethyldichlorosilane and other chlorosilanes. This residue consists of a large number of by-products such as for example $CH_3Cl_2SiSiCH_3Cl_2$, $CH_3Cl_2SiSi(CH_3)_2Cl$ and other disilanes of the formula $Si_2(CH_3)_xCl_{6-x}$ wherein x equals either 1, 2, or 3, as well as trisilanes of the formula $Si_3(CH_3)_xCl_{8-x}$, wherein x equals either 1, 2, 3, or 4, and minor amounts of disilylmethane structures such as $CH_3Cl_2SiCH_2SiCH_3Cl_2$ and lesser amounts of disilylethane structures such as $CH_3Cl_2SiCH_2CH_2SiCH_3Cl_2$ and small amounts of numerous organochlorosilanes of unproven structures. A typical high boiling residue from the methyl chloride direct process usually contains more than fifty percent by weight of chloride. A typical high boiling residue from the reaction with hydrogen chloride usually consists mostly of compounds of the type $Cl(HSiCl)_xCl$ wherein x=1,2,3, or 4, as well as $SiCl_4$.

Many attempts have been made to utilize these residues as they are otherwise waste products and have to be subjected to various treatments to neutralize them and then they are landfilled which can create certain environmental problems. All attempts at utilizing certain of the distillable products from the residue have led to products which are expensive and are based on a source which is inconsistent at best and therefore is not desirable for large volumes of materials.

The first step of the instant process, the reaction of the alcohol with the chloride of the chlorine-containing silicon compounds has been described as a continuous process for the conversion of monomeric chlorosilanes to monomeric alkoxysilanes in U.S. Pat. No. 4,506,087 which issued Mar. 19, 1985 to Fischer, et al. Therein is described a complicated process and apparatus which has been found useful for such a process. This reference, however, does not describe the entire process set forth in the instant invention, and it does not set forth the fact that complex mixtures of materials, including polysilanes, can be converted to monomeric alkoxysilanes by the instant process.

The instant invention overcomes the problems set forth above and provides an economical process for obtaining valuable monomeric silane intermediates as well as valuable recovery of hydrogen chloride and hydrogen.

THE INVENTION

This invention therefore deals with a process of recovering monomeric alkoxysilanes from mixtures of chlorine-containing silicon compounds wherein waste chlorine-containing silicon compounds are converted to useful, valuable silicon intermediates. It further provides for the recovery of valuable hydrogen chloride and hydrogen gas.

More specifically, this invention deals with a process for the recovery of monomeric alkoxysilanes from mixtures of chlorine-containing silicon compounds, the process comprising (A) contacting the mixture of chlorine-containing silicon compounds with a stoichiometric excess of a lower alcohol at a temperature above 20° C. to form a liquid mixture and heating the mixture to remove by-produced gaseous HCl; (B) contacting the products from (A) with a base at a temperature in excess of 20° C. to form essentially monomeric alkoxysilanes while removing by-produced hydrogen gas for a period of time required to remove essentially all of such by-produced hydrogen gas, whereby a mixture of predominantly monomeric alkoxysilanes are obtained.

DETAILED DESCRIPTION OF THE INVENTION

As was indicated above, this invention is a process for the recovery of monomeric alkoxysilanes and hydrogen chloride from mixtures of chlorine-containing silicon compounds.

The focus of such a process is directed to Direct Process Residues, but it can be applied to any mixture of chlorine-containing silicon compounds. Examples of such mixtures are set forth above and also included in such mixtures are small amounts of silicon compounds which have hydrogen substituted on silicon. For purposes of this invention, "chlorine-containing silicon compounds" includes those mixtures which not only contain chlorine and organic groups, but it also includes silanes having other groups substituted on silicon such as hydrogen of the type $H_ySi_xCl_{2x+2-y}$ where y=0, 1, 2, and 3 and x=2, 3, or 4 which are residues boiling above $Cl_3SiH$ (35° C.), which are obtained in the manufacture of $Cl_3SiH$ by reaction of hydrogen chloride with elemental silicon at elevated temperatures.

The processing equipment is not critical in this process and any equipment which is reliable, efficient and normally used in such reactions is useful herein, examples of such equipment being set forth in the examples.

The first step of the process, i.e., step (A) requires that the mixture of chlorine-containing silicon compounds be contacted with a lower alcohol. Such lower alcohols for purposes of this invention include those primary and secondary alcohols having from 1 to 6 carbon atoms and include, for example, primary alcohols such as methanol, ethanol and hexanol and secondary alcohols such as isopropanol. Preferred for this invention are the primary alcohols and most preferred alcohols are methanol and ethanol.

By "contacting", it is meant that the alcohol is added to the chlorine-containing silicon compounds and mixed together in any given manner such that there is intimate contact between the chlorine-containing silicon compounds and the alcohols. This mixing should be done at or above room temperature, preferably at the reflux temperature of the mixture of materials. When the mixing is carried out, the chlorine-containing silicon compounds react very rapidly with the alcohol and form mixed alkoxy silicon compounds and liberate hydrogen chloride essentially according to the following reaction scheme:

To add to the economies of the process, the hydrogen chloride, which is gaseous, is collected and either reused in related organosilicon processes, or is sold for other purposes. Essentially all of the chloride can be liberated as hydrogen chloride, depending upon how the alcohol is added to the chlorosilane and the temperature at which the process is carried out. The details of the ratios of alcohol to chloride, the temperatures and other significant factors regulating the evolution and collection of essentially all of the generated hydrogen chloride can be found in the above mentioned U.S. Patent, primarily at column 3.

The mixture of materials is heated during this step in order to expel hydrogen chloride from the mixture as rapidly as it is formed and to convert the chlorine-containing silicon compounds to alkoxy-containing silicon compounds and this heating is carried out generally at reflux of the materials. The mixture of alkoxy-containing silicon compounds after one equivalent of alcohol per equivalent of chloride has been added are essentially the alkoxy equivalents of the chlorine-containing compounds of the starting material.

In the second step of this process, the mixture of alkoxy-containing silicon compounds obtained by the previous step are further treated in solution with a base. Upon contact with the base, the alkoxy-containing silicon compounds are rapidly converted to monomeric alkoxysilanes it being understood that any such monomeric alkoxysilanes in the solution are not affected and they just ride through this step essentially without change.

Examples of some of the reactions during this step are for example,

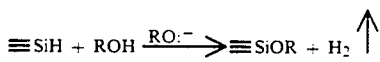

Also, any di- or polysilane that is present is oxidized viz.

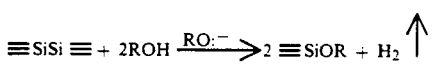

Bases useful in the process disclosed herein are alkali metal bases from the metals found in Group Ia of the periodic table. Preferred are the sodium, potassium and lithium metal bases. Especially preferred are the sodium and potassium bases because they are strong bases and are readily available for use in this process. Thus, sodium ethoxide and potassium ethoxide as well as their methoxide equivalents are useful for this process.

This step of the process requires that the solution and the base be contacted at a temperature in the range of 20° C. to 100° C. for a period of time of about 1 minute to ½ hour. Since these reactions are nearly quantitative and go to completion in minutes near room temperature, it is preferred that the reaction be carried out in a range at or near room temperature to about 75° C.

It should be recognized by those skilled in the art that when the reaction is exothermic, one must take precautions at the incipient stages to prevent the reaction from overheating. Control of the reaction will allow the materials of the reaction to be blended together without undue heating. One of the best means for controlling the exotherm and prevent undue heating is to add the base into the solution of silicon compounds at a slow rate.

Hydrogen gas is by-produced by this reaction and such gas can be captured, or it can be allowed to excape. One of the convenient ways to determine the endpoint of the reaction is to observe the absence of hydrogen gas evolution.

The products that are obtained by this process are monomeric alkoxy silanes. The term "monomeric" refers to molecules having only one silicon atom. In this case, the silanes can be a mixture as regards how many alkoxy groups are on silicon and also, depending on the base that is used, the silanes can be mixtures of the types of alkoxy groups on silicon as well.

Once the reaction with the base is finished, the solution is distilled to recover the individual monomeric alkoxysilanes.

Now so that those skilled in the art can further appreciate this invention the following examples are presented.

EXAMPLE 1

Absolute ethanol (329 g) was pumped at a rate of 2 ml/min below the surface of Cl$_3$SiH/Direct Process Residue (390 g) which was situated in a 1-liter, round-bottomed, three-necked, glass flask. The residue contained 52 weight percent Cl. The addition was make at room temperature (25° C.). After the end of the addition of the alcohol, the temperature of the liquid was slowly raised to reflux. Hydrogen chloride (192.3 g) was expelled from the mixture, which accounted for 95% of the original chloride in the residue.

Next, sodium ethoxide (21 weight percent dissolved in ethanol) was slowly added into the refluxing liquid until the evolution of hydrogen ceased. The mixture was then distilled. Recovered were 281 g of ethanol (b.p. 78° C.) followed by 302 g of tetraethoxysilane (b.p. 155° C.), leaving only a small amount of dry solid residue in the flask.

EXAMPLE 2

Methanol (330 g) was pumped at a rate of 10 ml/min below the surface of 563 g of the same Direct Process Residue as was used in example 1, using the same type of apparatus. After the addition of the methanol at room temperature, 261 g of hydrogen chloride had been expelled from the system without further heating, 86% of the original chloride.

Thereafter, sodium methoxide (25% in methanol) (175 g) was added and the mixture was distilled. Methanol, (b.p. 64° C., 164 g) was recovered followed by tetramethoxysilane, (b.p. 104° C., 270 g) leaving only a dry solid residue in the flask. No other silicon compounds could be detected in the distillate by gas liquid chromatography.

EXAMPLE 3

Methanol (425 g) was pumped beneath the surface of stirred dimethyl-Direct Process Residue (804.5 g) (46 weight percent chloride) at about 60° C. in a three-necked, two liter round bottomed glass flask and hydrogen chloride was permitted to escape through a distillation head until 338 g (91%) of the original chloride was expelled from the reaction mass. Then sodium methoxide (25 weight % in methanol, 606 g) was added to the mixture at 60° C., causing rapid evolution of hydrogen and the mixture was then distilled to a pot temperature of 250° C. The distillate was methanol (588 g); b.p. 64°; dimethyldimethoxysilane (56 g); b.p. 82°; methyltrimethoxysilane (259 g); b.p. 104°; higher boiling liquid (75 g). The higher boiling liquid is believed to be a mixture of disilmethylene compounds of the formula $(CH_3)_x(CH_3O)_{3-x}SiCH_2Si(CH_3)_x(CH_3O)_{3-x}$ wherein $x=1$ or 2.

That which is claimed is:

1. A process for the recovery of monomeric alkoxy silanes from mixtures of chlorine-containing silicon compounds, the process comprising:
   (A) contacting the mixture of chlorine-containing silicon compounds with a stoichiometric excess of a lower alcohol at a temperature above 20° C. to form a liquid mixture and heating the mixture to remove by-produced gaseous HCl;
   (B) contacting the products from (A) with a base at a temperature in excess of 20° C. to form essentially monomeric alkoxysilanes while removing by-produced hydrogen gas for a period of time required to remove essentially all of such by-produced hydrogen gas, whereby a mixture of predominantly monomeric alkoxysilanes is obtained.

2. A process as claimed in claim 1 in which the product of (B) is further subjected to distillation to separate and collect monomeric alkoxysilanes.

3. A process as claimed in claim 1 wherein in step (A), mixtures of $Cl(SiCl_{2-x}H_x)_yCl$ wherein x equals 0 or 1 and y equals 1 to 4, are contacted with ethanol and in step (B), the mixture of (A) is contacted with sodium ethoxide.

4. A process as claimed in claim 1 wherein in step (A), mixtures of $Cl(SiCl_{2-x}H_x)_yCl$ wherein x equals 0 or 1 and y equals 1 to 4, are contacted with methanol and in step (B), the mixture of (A) is contacted with sodium methoxide.

5. A process as claimed in claim 1 wherein in step (A), mixtures of $Cl\{Si(CH_3)_xCl_{(2-x)}\}_yCl$ wherein x equals 1 or 2 and y equals 1 to 4, are contacted with methanol.

6. A process as claimed in claim 1 wherein in step (A), mixtures of $Cl\{Si(CH_3)_xCl_{(2-x)}\}_yCl$ wherein x equals 1 or 2 and y equals 1 to 4, are contacted with ethanol.

* * * * *